(12) United States Patent
Rowe

(10) Patent No.: US 7,347,365 B2
(45) Date of Patent: Mar. 25, 2008

(54) COMBINED TOTAL-INTERNAL-REFLECTANCE AND TISSUE IMAGING SYSTEMS AND METHODS

(75) Inventor: Robert K. Rowe, Corrales, NM (US)

(73) Assignee: Lumidigm, Inc., Albuquerque, NM (US)

( * ) Notice: Subject to any disclaimer, the term of this patent is extended or adjusted under 35 U.S.C. 154(b) by 202 days.

(21) Appl. No.: 11/015,732

(22) Filed: Dec. 17, 2004

(65) Prior Publication Data

US 2005/0205667 A1  Sep. 22, 2005

Related U.S. Application Data

(63) Continuation-in-part of application No. 10/818,698, filed on Apr. 5, 2004.

(60) Provisional application No. 60/552,662, filed on Mar. 10, 2004, provisional application No. 60/504,594, filed on Sep. 18, 2003, provisional application No. 60/483,281, filed on Jun. 27, 2003, provisional application No. 60/460,247, filed on Apr. 4, 2003.

(51) Int. Cl.
*G06K 5/00* (2006.01)

(52) U.S. Cl. ............... 235/382; 382/115; 382/191

(58) Field of Classification Search ........ 235/382; 382/115, 191
See application file for complete search history.

(56) References Cited

U.S. PATENT DOCUMENTS

| 3,508,830 | A | 4/1970 | Hopkins et al. |
|---|---|---|---|
| 3,872,443 | A | 3/1975 | Ott |
| 3,910,701 | A | 10/1975 | Henderson et al. |
| RE29,008 | E | 10/1976 | Ott |
| 4,035,083 | A | 7/1977 | Woodriff et al. |
| 4,142,797 | A | 3/1979 | Astheimer |
| 4,169,676 | A | 10/1979 | Kaiser |
| 4,170,987 | A * | 10/1979 | Anselmo et al. ............ 600/475 |
| 4,260,220 | A | 4/1981 | Whitehead |
| 4,427,889 | A | 1/1984 | Muller |

(Continued)

FOREIGN PATENT DOCUMENTS

EP  0 280 418 A1  8/1988

(Continued)

OTHER PUBLICATIONS

Bantle, John P. & Thomas, William, "Glucose Measurement in Patients with Diabetes Mellitus with Dermal Interstitial Fluid," Copyright © 1997 by Mosby-Year Book, Inc., 9 pages.

(Continued)

*Primary Examiner*—Uyen-Chau N Le
(74) *Attorney, Agent, or Firm*—Townsend and Townsend and Crew LLP

(57) ABSTRACT

Methods and systems are provided for combining total-internal-reflectance and tissue imaging to perform biometric functions. The system may include an illumination source, a platen, a light detector, an optical train, and a computational unit. The platen is disposed to make contact with a skin site of an individual. The optical train is disposed to provide optical paths between the illumination source and the platen, and between the platen and the light detector. The combination of the illumination source and optical train provides illumination to the platen under multispectral conditions. The computational unit is interfaced with the light detector and has instructions to generate a total-internal-reflectance image of the skin site from a first portion of light received from the skin site, and to generate a tissue image of the skin site from a second portion of light received from the skin site.

25 Claims, 8 Drawing Sheets
(1 of 8 Drawing Sheet(s) Filed in Color)

U.S. PATENT DOCUMENTS

| | | |
|---|---|---|
| 4,537,484 A | 8/1985 | Fowler |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |
| 4,657,397 A | 4/1987 | Oehler et al. |
| 4,661,706 A | 4/1987 | Messerschmidt et al. |
| 4,684,255 A | 8/1987 | Ford |
| 4,712,912 A | 12/1987 | Messerschmidt |
| 4,730,882 A | 3/1988 | Messerschmidt |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,936,680 A | 6/1990 | Henkes et al. |
| 4,944,021 A | 7/1990 | Hoshino et al. |
| 4,975,581 A | 12/1990 | Robinson et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,068,536 A | 11/1991 | Rosenthal |
| 5,070,874 A | 12/1991 | Barnes et al. |
| 5,158,082 A | 10/1992 | Jones |
| 5,163,094 A | 11/1992 | Prokoski et al. |
| 5,178,142 A | 1/1993 | Harjunmaa et al. |
| 5,179,951 A | 1/1993 | Knudson |
| 5,204,532 A | 4/1993 | Rosenthal |
| 5,222,495 A | 6/1993 | Clarke et al. |
| 5,222,496 A | 6/1993 | Clarke et al. |
| 5,223,715 A | 6/1993 | Taylor |
| 5,225,678 A | 7/1993 | Messerschmidt |
| 5,230,702 A | 7/1993 | Lindsay et al. |
| 5,237,178 A | 8/1993 | Rosenthal et al. |
| 5,243,546 A | 9/1993 | Maggard |
| 5,257,086 A | 10/1993 | Fateley et al. |
| 5,267,152 A | 11/1993 | Yang et al. |
| 5,268,749 A | 12/1993 | Weber et al. |
| 5,291,560 A | 3/1994 | Daugman |
| 5,299,570 A | 4/1994 | Hatschek |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,348,003 A | 9/1994 | Caro |
| 5,351,686 A | 10/1994 | Steuer et al. |
| 5,355,880 A | 10/1994 | Thomas et al. |
| 5,360,004 A | 11/1994 | Purdy et al. |
| 5,361,758 A | 11/1994 | Hall et al. |
| 5,366,903 A | 11/1994 | Lundsgaard et al. |
| 5,372,135 A | 12/1994 | Mendelson et al. |
| 5,379,764 A | 1/1995 | Barnes et al. |
| 5,402,778 A | 4/1995 | Chance |
| 5,405,315 A | 4/1995 | Khuri et al. |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,505,726 A | 4/1996 | Meserol |
| 5,507,723 A | 4/1996 | Keshaviah |
| 5,515,847 A | 5/1996 | Braig et al. |
| 5,518,623 A | 5/1996 | Keshaviah et al. |
| 5,523,054 A | 6/1996 | Switalski et al. |
| 5,533,509 A | 7/1996 | Koashi et al. |
| 5,537,208 A | 7/1996 | Bertram et al. |
| 5,539,207 A | 7/1996 | Wong et al. |
| 5,552,997 A | 9/1996 | Massart |
| 5,559,504 A | 9/1996 | Itsumi et al. |
| 5,596,992 A | 1/1997 | Haaland et al. |
| 5,606,164 A | 2/1997 | Price et al. |
| 5,630,413 A | 5/1997 | Thomas et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,681,273 A | 10/1997 | Brown |
| 5,708,593 A | 1/1998 | Saby et al. |
| 5,719,399 A | 2/1998 | Alfano et al. |
| 5,719,950 A | 2/1998 | Osten et al. |
| 5,724,268 A | 3/1998 | Sodickson et al. |
| 5,743,262 A | 4/1998 | Lepper, Jr. et al. |
| 5,747,806 A | 5/1998 | Khalil |
| 5,750,994 A | 5/1998 | Schlager |
| 5,751,835 A | 5/1998 | Topping et al. |
| 5,761,330 A | 6/1998 | Stoianov et al. |
| 5,782,755 A | 7/1998 | Chance et al. |
| 5,792,050 A | 8/1998 | Alam et al. |
| 5,792,053 A | 8/1998 | Skladner et al. |
| 5,793,881 A | 8/1998 | Stiver et al. |
| 5,796,858 A | 8/1998 | Zhou et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,857,462 A | 1/1999 | Thomas et al. |
| 5,860,421 A | 1/1999 | Eppstein et al. |
| 5,867,265 A | 2/1999 | Thomas |
| 5,886,347 A | 3/1999 | Inoue et al. |
| 5,902,033 A | 5/1999 | Levis et al. |
| 5,914,780 A | 6/1999 | Turner et al. |
| 5,929,443 A | 7/1999 | Alfano et al. |
| 5,933,792 A | 8/1999 | Andersen et al. |
| 5,935,062 A | 8/1999 | Messerschmidt et al. |
| 5,945,676 A | 8/1999 | Khalil |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 5,987,346 A | 11/1999 | Benaron et al. |
| 5,999,637 A | 12/1999 | Toyoda et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A | 2/2000 | Amerov et al. |
| 6,028,773 A | 2/2000 | Hundt |
| 6,031,609 A | 2/2000 | Funk et al. |
| 6,034,370 A | 3/2000 | Messerschmidt |
| 6,040,578 A | 3/2000 | Malin et al. |
| 6,041,247 A | 3/2000 | Weckstrom et al. |
| 6,041,410 A | 3/2000 | Hsu et al. |
| 6,043,492 A | 3/2000 | Lee et al. |
| 6,044,285 A | 3/2000 | Chaiken et al. |
| 6,045,502 A | 4/2000 | Eppstein et al. |

| | | |
|---|---|---|
| 6,046,808 A | 4/2000 | Fately |
| 6,049,727 A | 4/2000 | Crothall |
| 6,056,738 A | 5/2000 | Marchitto et al. |
| 6,057,925 A | 5/2000 | Anthon |
| 6,061,581 A | 5/2000 | Alam et al. |
| 6,061,582 A | 5/2000 | Small et al. |
| 6,066,847 A | 5/2000 | Rosenthal |
| 6,069,689 A | 5/2000 | Zeng et al. |
| 6,070,093 A | 5/2000 | Oosta et al. |
| 5,737,439 A | 6/2000 | Lapsley et al. |
| 6,073,037 A | 6/2000 | Alam et al. |
| 6,081,612 A * | 6/2000 | Gutkowicz-Krusin et al. .................... 382/128 |
| 6,088,605 A | 7/2000 | Griffith et al. |
| 6,088,607 A | 7/2000 | Diab et al. |
| 6,097,035 A | 8/2000 | Belongie et al. |
| 6,100,811 A | 8/2000 | Hsu et al. |
| 6,115,484 A | 9/2000 | Bowker et al. |
| 6,115,673 A | 9/2000 | Malin et al. |
| 6,122,042 A | 9/2000 | Wunderman et al. |
| 6,122,394 A | 9/2000 | Neukermans et al. |
| 6,122,737 A | 9/2000 | Bjorn et al. |
| 6,125,192 A | 9/2000 | Bjorn et al. |
| 6,141,101 A | 10/2000 | Bleier et al. |
| 6,147,749 A | 11/2000 | Kubo et al. |
| 6,148,094 A | 11/2000 | Kinsella |
| 6,152,876 A | 11/2000 | Robinson et al. |
| 6,154,658 A | 11/2000 | Caci |
| 6,157,041 A | 12/2000 | Thomas et al. |
| 6,159,147 A | 12/2000 | Lichter et al. |
| 6,172,743 B1 | 1/2001 | Kley et al. |
| 6,175,407 B1 | 1/2001 | Sartor |
| 6,181,414 B1 | 1/2001 | Raz et al. |
| 6,181,958 B1 | 1/2001 | Steuer et al. |
| 6,188,781 B1 | 2/2001 | Brownlee |
| 6,212,424 B1 | 4/2001 | Robinson |
| 6,226,541 B1 | 5/2001 | Eppstein et al. |
| 6,230,034 B1 | 5/2001 | Messerschmidt et al. |
| 6,240,306 B1 | 5/2001 | Rohrscheib et al. |
| 6,240,309 B1 | 5/2001 | Yamashita et al. |
| 6,241,663 B1 | 6/2001 | Wu et al. |
| 6,256,523 B1 | 7/2001 | Diab et al. |
| 6,272,367 B1 | 8/2001 | Chance |
| 6,280,381 B1 | 8/2001 | Malin et al. |
| 6,282,303 B1 | 8/2001 | Brownlee |
| 6,285,895 B1 | 9/2001 | Ristolainen et al. |
| 6,292,576 B1 | 9/2001 | Brownlee |
| 6,301,815 B1 | 10/2001 | Sliwa |
| 6,304,767 B1 | 10/2001 | Soller et al. |
| 6,307,633 B1 | 10/2001 | Mandella et al. |
| 6,309,884 B1 | 10/2001 | Cooper et al. |
| 6,317,507 B1 | 11/2001 | Dolfing |
| 6,324,310 B1 | 11/2001 | Brownlee |
| 6,330,346 B1 | 12/2001 | Peterson et al. |
| 6,404,904 B1 | 6/2002 | Einighammer et al. |
| 6,483,929 B1 | 11/2002 | Murakami et al. |
| 6,504,614 B1 | 1/2003 | Messerschmidt et al. |
| 6,560,352 B2 | 5/2003 | Rowe et al. |
| 6,574,490 B2 | 6/2003 | Abbink et al. |
| 6,628,809 B1 | 9/2003 | Rowe et al. |
| 6,741,729 B2 | 5/2004 | Bjorn et al. |
| 6,799,275 B1 | 9/2004 | Bjorn |
| 6,816,605 B2 | 11/2004 | Rowe et al. |
| 2002/0171834 A1 | 11/2002 | Rowe et al. |
| 2002/0183624 A1 | 12/2002 | Rowe et al. |
| 2003/0044051 A1 | 3/2003 | Fujieda |
| 2003/0078504 A1 | 4/2003 | Rowe et al. |
| 2004/0047493 A1 | 3/2004 | Rowe et al. |
| 2004/0240712 A1 | 12/2004 | Rowe et al. |
| 2005/0007582 A1 | 1/2005 | Villers et al. |
| 2005/0185847 A1 | 8/2005 | Rowe |
| 2005/0265585 A1 | 12/2005 | Rowe |
| 2005/0265586 A1 | 12/2005 | Rowe et al. |
| 2005/0271258 A1 | 12/2005 | Rowe |
| 2006/0002597 A1 | 1/2006 | Rowe |
| 2006/0002598 A1 | 1/2006 | Rowe et al. |

FOREIGN PATENT DOCUMENTS

| | | |
|---|---|---|
| EP | 0 897 164 A2 | 2/1999 |
| EP | 0 924 656 A2 | 6/1999 |
| WO | WO 92/17765 A1 | 10/1992 |
| WO | WO 93/07801 A1 | 4/1993 |
| WO | WO 01/18332 A1 | 3/2001 |
| WO | WO 01/27882 A2 | 4/2001 |
| WO | WO 01/52180 A1 | 7/2001 |
| WO | WO 01/52726 A1 | 7/2001 |
| WO | WO 01/53805 A1 | 7/2001 |
| WO | WO 02/084605 A2 | 10/2002 |
| WO | WO 02/099393 A2 | 12/2002 |
| WO | WO 2004/068388 A2 | 8/2004 |
| WO | WO 2004/068394 A1 | 8/2004 |

OTHER PUBLICATIONS

Berkoben et al., "Vascular Access for Hemodialysis", Clinical Dialysis, published on or before Oct. 30, 1997, 20 pages.

Bleyer et al., "The costs of Hospitalizations Due to Hemodialysis Access Management", Nephrology News & Issues, Jan. 1995, pp. 19, 20 and 22.

Brochure entitled "Determination of Delivered Therapy Through Measurement of Effective Clearance", Fresenius USA, Dec. 1994, 1 page.

Daugirdas et al., "Comparison of Methods to Predict the Equilibrated Kt/V (eKt/V) in the Hemo Study", National Institutes of Health, NIDDK, Bethesda, MD, Aug. 20, 1996.

Demos, S.G. & Alfano R.R. "Optical fingerprinting using polarisation contrast improvement" Electronics Letters, Mar. 27, 1997, pp. 582-584, vol. 33, No. 7.

Depner et al., "Clinical Measurement of Blood Flow in Hemodialysis Access Fistulae and Grafts by Ultrasound Dilution", from the Department of Nephrology, University of California, published on or before Oct. 30, 1997, 4 pages.

Hakim et al., "Effects of Dose of Dialysis on Morbidity and Mortality", American Journal of Kidney Diseases, vol. 23, No. 5, May 1994, pp. 661-669.

Jacobs, et al., "A Disposable Urea Sensor for Continuous Monitoring of Hemodialysis Efficiency", USAIO Journal, 1993, pp. M353-M358.

Keshaviah et al., "On-line monitoring of the delivery of the hemodialysis prescription", Pediatric Nephrology, vol. 9, 1995, pp. S2-S8.

Krivitski, "Theory and Validation of Access Flow Measurement by Dilution Technique During Hemodialysis", Kidney International, vol. 48, 1995, pp. 244-250.

Marbach, Ralf, "Measurement Techniques for IR Spectroscopic Blood Glucose Determination," (1994) pp. 1-158.

Mardia, K.V. et al., Multivariate Analysis, Academic Press (1979) pp. 300-325.

Nichols, et al., "Design and Testing of a White-Light, Steady-State Diffuse Reflectance Spectrometer for Determination of Optical Properties of Highly Scattering Systems," Applied Optics, Jan. 1, 1997, 36(1), pp. 93-104.

Ripley, B.D., Pattern Recognition and Neural Networks, Cambridge University Press (1996) pp. 91-120.

Ronco et al., "On-line urea monitoring: a further step towards adequate dialysis prescription and delivery", Int'l. Journal of Artificial Organs, vol. 18, No. 9, 1995, pp. 534-543.

Service, F. John et al., "Dermal Interstitial Glucose as an Indicator of Ambient Glycemia," Diabetes Care, vol. 20, No. 9, Sep. 1997, 9 pages.

Sherman, "Recirculation in the Hemodialysis Access", Principles and Practice of Dialysis, 1994, pp. 38-46.

Sherman, "The Measurement of Dialysis Access Recirculation", American Journal of Kidney Diseases, vol. 22, No. 4, Oct. 1993, pp. 616-621.

Steuer et al., "A New Optical Technique for Monitoring Hematocrit and Circulating Blood Volume: Its Application in Renal Dialysis", Dialysis & Transplantation, vol. 22, No. 5, May 1993, pp. 260-265.

Webb, Paul, "Temperatures of Skin, Subcutaneous Tissue, Muscle and Core in Resting Men in Cold, Comfortable and Hot Conditions," European Journal of Applied Physiology, vol. 64 (1992) pp. 471-476.

Zavala, Albert & Paley, James J. "Using fingerprint measures to predict other anthropometric Variables" Human Factors, 1975, pp. 591-602, vol. 17, No. 6.

* cited by examiner

 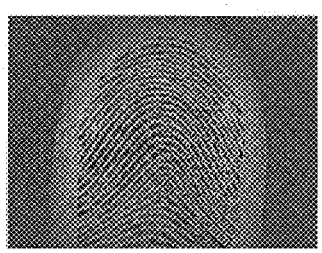 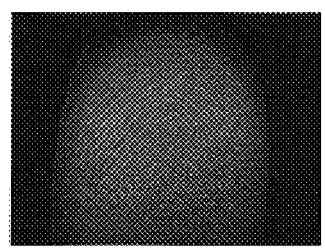
Fig. 8A     Fig. 8B     Fig. 8C
 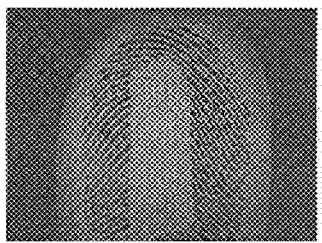 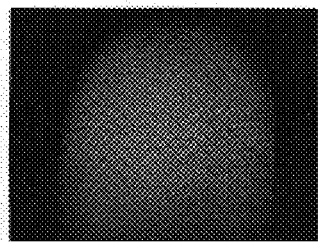
Fig. 9A     Fig. 9B     Fig. 9C
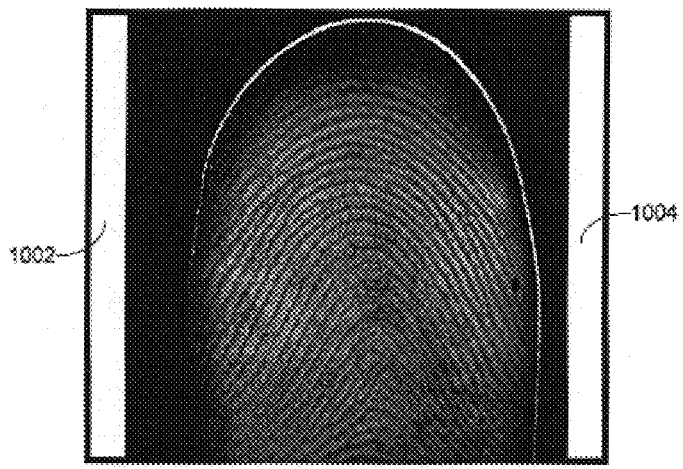
Fig. 10

COMBINED TOTAL-INTERNAL-REFLECTANCE AND TISSUE IMAGING SYSTEMS AND METHODS

CROSS-REFERENCES TO RELATED APPLICATIONS

This application is a continuation-in-part of U.S. patent application Ser. No. 10/818,698, entitled "MULTISPECTRAL BIOMETRIC SENSOR," filed Apr. 5, 2004 by Robert K. Rowe et al., which is a nonprovisional of U.S. Prov. Pat. Appl. No. 60/460,247, entitled "NONINVASIVE ALCOHOL MONITOR," filed Apr. 4, 2003; U.S. Prov. Pat. Appl. No. 60/483,281, entitled "HYPERSPECTRAL FINGERPRINT READER," filed Jun. 27, 2003 by Robert K. Rowe et al.; U.S. Prov. Pat. Appl. No. 60/504,594, entitled "HYPERSPECTRAL FINGERPRINTING," filed Sep. 18, 2003; and U.S. Prov. Pat. Appl. No. 60/552,662, entitled "OPTICAL SKIN SENSOR FOR BIOMETRICS," filed Mar. 10, 2004.

This application is also related to commonly assigned U.S. patent application Ser. No. 09/874,740, entitled "APPARATUS AND METHOD OF BIOMETRIC DETERMINATION USING SPECIALIZED OPTICAL SPECTROSCOPY SYSTEM," filed Jun. 5, 2001.

The entire disclosure of each application identified above is incorporated herein by reference for all purposes.

BACKGROUND OF THE INVENTION

This application relates generally to biometrics. More specifically, this application relates to combined total-internal-reflectance and tissue imaging systems and methods.

"Biometrics" refers generally to the statistical analysis of characteristics of living bodies. One category of biometrics includes "biometric identification," which commonly operates under one of two modes to provide automatic identification of people or to verify purported identities of people. Biometric sensing technologies measure the physical features or behavioral characteristics of a person and compare those features to similar prerecorded measurements to determine whether there is a match. Physical features that are commonly used for biometric identification include faces, irises, hand geometry, vein structure, and fingerprint patterns, which is the most prevalent of all biometric-identification features. Current methods for analyzing collected fingerprints include optical, capacitive, radio-frequency, thermal, ultrasonic, and several other less common techniques.

Most of the fingerprint-collection methods rely on measuring characteristics of the skin at or very near the surface of a finger. In particular, optical fingerprint readers typically rely on the presence or absence of a difference in the index of refraction between the sensor platen and the finger placed on it. When an air-filled valley of the fingerprint is above a particular location of the platen, total internal reflectance ("TIR") occurs in the platen because of the air-platen index difference. Alternatively, if skin of the proper index of refraction is in optical contact with the platen, then the TIR at this location is "frustrated," allowing light to traverse the platen-skin interface or, in some arrangements, allowing the light to traverse the interface at an angle that is unavailable when TIR phenomena are present at the location. A map of the differences in TIR across the region where the finger is touching the platen forms the basis for a conventional optical fingerprint reading. There are a number of optical arrangements used to detect this variation of the optical interface in both bright-field and dark-field optical arrangements. Commonly, a single, quasimonochromatic beam of light is used to perform this TIR-based measurement.

There also exists non-TIR optical fingerprint sensors. In most cases, these sensors rely on some arrangement of quasimonochromatic light to illuminate the front, sides, or back of a fingertip, causing the light to diffuse through the skin. The fingerprint image is formed due to the differences in light transmission across the skin-platen boundary for the ridge and valleys. The difference in optical transmission are due to changes in the Fresnel reflection characteristics due to the presence or absence of any intermediate air gap in the valleys, as known to one of familiarity in the art.

Although TIR fingerprint sensors are the most common form of optical fingerprint readers, they are particularly susceptible to image quality problems due to non-ideal conditions. If the skin is overly dry, the index match with the platen will be compromised, resulting in poor image contrast. Similarly, if the finger is very wet, the valleys may fill with water, causing an optical coupling to occur all across the fingerprint region and greatly reducing image contrast. Similar effects may occur if the pressure of the finger on the platen is too little or too great, the skin or sensor is dirty, the skin is aged and/or worn, or overly fine features are present such as may be the case for certain ethnic groups and in very young children. These effects decrease image quality and thereby decrease the overall performance of the fingerprint sensor. In some cases, commercial optical fingerprint readers incorporate a thin membrane of soft material such as silicone to help mitigate these effects and restore performance. As a soft material, the membrane is subject to damage, wear, and contamination, limiting the use of the sensor without maintenance and limiting the environments in which the sensor can be used.

Biometric sensors, particularly fingerprint biometric sensors, are generally prone to being defeated by various forms of spoof samples. In the case of fingerprint readers, a variety of methods are known in the art for presenting readers with a fingerprint pattern of an authorized user that is embedded in some kind of inanimate material such as paper, gelatin, epoxy, latex, and the like. Thus, even if a fingerprint reader can be considered to reliably determine the presence or absence of a matching fingerprint pattern, it is also critical to the overall system security to ensure that the matching pattern is being acquired from a genuine, living finger, which may be difficult to ascertain with many common sensors.

Another way in which some biometric systems may be defeated is through the use of a replay attack. In this scenario, an intruder records the signals coming from the sensor when an authorized user is using the system. At a later time, the intruder manipulates the sensor system such that the prerecorded authorized signals may be injected into the system, thereby bypassing the sensor itself and gaining access to the system secured by the biometric.

There is accordingly a general need in the art for improved methods and systems for biometric sensing.

BRIEF SUMMARY OF THE INVENTION

Embodiments of the invention provide methods and systems for combining total-internal-reflectance and tissue imaging to perform biometric functions. In one set of embodiments, a system is provided for performing a biometric function. The system comprises an illumination source, a platen, a light detector, an optical train, and a computational unit. The platen is disposed to make contact with a skin site of an individual. The optical train is disposed to provide optical paths between illumination source and platen and between the platen and the light detector. The combination of the illumination source and optical train provides illumination to the platen under multispectral conditions. The computational unit is interfaced with the light detector and has instructions to generate a total-internal-reflectance image of the skin site from a first portion of light received from the skin site, and to generate a multispectral tissue image of the skin site from a second portion of light received from the skin site.

In some embodiments, the illumination source may be polychromatic illumination source. In some cases, the optical train comprises a prism having a plurality of facets, with the illumination source disposed to provide illumination light to a first of the facets and the light detector disposed to receive light from a second of the facets. In a specific embodiment, the first and second facets are the same facet. In other embodiments, the light detector comprises a first light detector disposed to receive the first portion of light through the second facet and a second light detector disposed to receive the second portion of light from a third facet. The second facet may be substantially orthogonal to a first axis having an angle with the platen greater than a critical angle $\theta_c$ of an interface with the platen and the air. The third facet may be substantially orthogonal to a second axis having an angle with the platen less than the critical angle $\theta_c$. In a specific embodiment, the first, second, and third facets are different facets. In some instances a diffuse reflector may be disposed on a fourth facet different from the first, second, and third facets. In other instances, a light absorber may be disposed on a fourth facet different from the first, second, and third facets.

In some embodiments, the light may be polarized. For instance, the optical train may comprise polarizers disposed to polarize light incident on the skin site and to polarize light received by the light detector. In one embodiment, the polarizers are oriented such that light incident on the skin site and the light received by the light detector have substantially parallel polarizations. In another embodiment, the polarizers are oriented such that light incident on the skin site and the light received by the light detector have substantially orthogonal polarizations.

In a second set of embodiments, a method is provided for performing a biometric function. A skin site of an individual is illuminated under multispectral conditions. Light is received from the skin site. A total-internal-reflectance image of the skin site is generated from a first portion of the received light. A multispectral tissue image of the skin site is generated from a second portion of the scattered light.

In different embodiments, the skin site may be illuminated with polychromatic light, which may be provided in some cases with a single illumination source. In one embodiment, the skin site is illuminated by generating light and directing the generated light to the skin site and to a diffuse reflector to provide a diffuse light field. In this embodiment, the total-internal-reflectance image of the skin site is generated by identifying dark patterns corresponding to positions where the skin site makes optical contact with the light and absorbs light. In another embodiment, the skin site is illuminated by generating light and directing the generated light to the skin site and to a light absorber. In this embodiment, the total-internal-reflectance image of the skin site comprises identifying illuminated patterns corresponding to positions where the skin site makes optical contact with the light and re-emits light.

In some embodiments, the skin site is in contact with a platen that defines a platen-air interface having a critical angle $\theta_c$. The first portion of light is received with a first detector disposed on a first axis having an angle with the platen-air interface greater than $\theta_c$. The second portion of light is received with a second detector disposed on a second axis having an angle with the platen-air interface less than $\theta_c$.

In some instances, illuminating the skin site may include polarizing generated light and polarizing the second portion of the received light. The polarizations of the generated and second portion of the received light may be substantially parallel or may be substantially orthogonal in different embodiments. In one embodiment where the generated and second portion of the received light have a first relative polarization, the steps of illuminating the skin site, receiving light from the skin site, generating the total-internal-reflectance image, and generating the multispectral tissue image are repeated with a different relative polarization between the generated light and second portion of the received light. In still other embodiments, illuminating the skin site may include polarizing generated light and polarizing the first portion of the received light with a polarization substantially parallel to a polarization of the generated light.

A perfusion change in skin may be identified by repeating the steps of illuminating the skin site and receiving light from the skin site to generate a second multispectral tissue image. Examples of biometric functions that may be performed include determining a liveness state of tissue at the skin site from the tissue image and verifying an identity of the individual by confirming consistency of the total-internal-reflectance image and of the tissue image with previously collected enrollment data.

In a third set of embodiments, a method is provided for performing a biometric function. A first image of a skin site of an individual is captured under a first set of optical conditions. A second image of the skin site is captured under a second set of optical conditions different from the first set. The first and second images are used to perform the biometric function. In one embodiment, the first and second set of optical conditions define different wavelengths of light incident on the skin site. In another embodiment, the first and second set of optical conditions define different polarization states.

BRIEF DESCRIPTION OF THE DRAWINGS

The file of this patent contains at least one drawings executed in color. Copies of this patent with color drawings will be provided by the Patent and Trademark Office upon request and payment of the necessary fee.

A further understanding of the nature and advantages of the present invention may be realized by reference to the remaining portions of the specification and the drawings wherein like reference labels are used throughout the several drawings to refer to similar components.

FIGS. 8A-8C are images generated with the methods and systems of the invention;

FIGS. 9A-9C are images generated with the methods and systems of the invention when part of a skin surface is obstructed; and FIG. 10 illustrates the use of optical reference material in some embodiments.

DETAILED DESCRIPTION OF THE INVENTION

Figure 1:
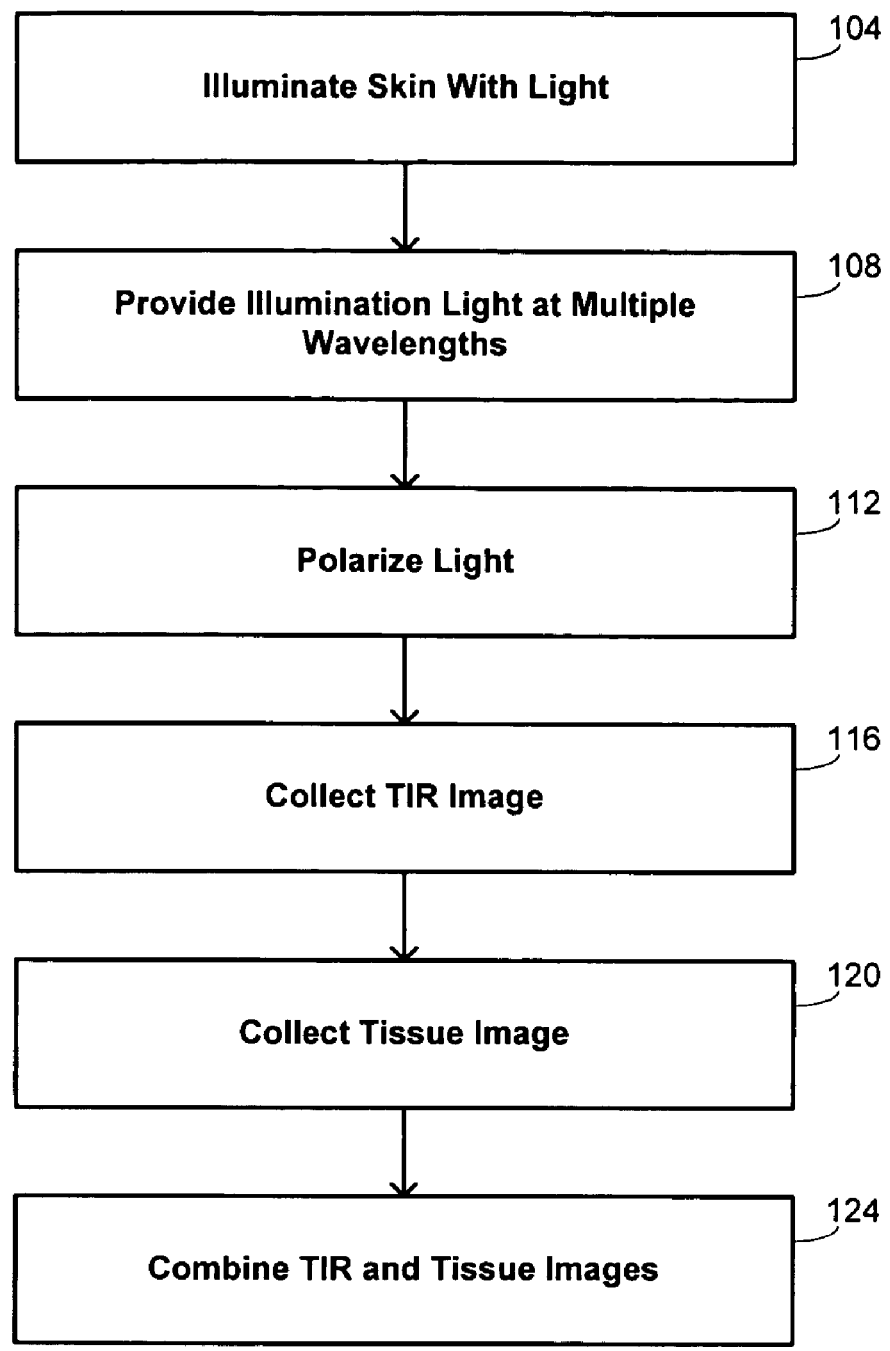
FIG. 1 is a flow diagram that summarizes aspects of several embodiments of the invention.

Embodiments of the invention provide systems that may combine TIR and tissue imaging systems. The TIR component examines the optical interface between skin and a platen, thereby providing a map outlining regions of contact and regions without contact. The tissue-imaging component results from measurements of light that scatter within tissue below the surface of the skin. In some embodiments, the wavelength ranges comprise the ultraviolet, visible, very-near-infrared, or near-infrared ranges, or combinations of these ranges. Embodiments of the invention collect images taken under a plurality of optical conditions, such as with different wavelengths and/or polarization conditions. Such embodiments are referred to herein as providing "multispectral" optical conditions, as may be provided by using polychromatic illumination sources, including polarizing elements in optical trains used to direct light, and the like. Collection of multispectral data is advantageously robust to non-ideal skin qualities, such as dryness, lack of resilience, and/or worn features such as are typically associated with the elderly, those who perform significant manual labor, or those whose skin is exposed to chemicals, such as hairdressers or nurses. The combined TIR and tissue images may be used for performing "biometric functions," which are intended to refer broadly to any function involving a biometric characterization, including biometric identification, biometric verification, liveness determinations, and the like.

Each component of the systems advantageously provides information not readily available with the other, with the combination synergistically providing more robust performance over a wider range of environmental and skin conditions than with either component alone. In addition, the combination presents greater spoof-detection and biometric capabilities by providing an ability to image subsurface features. Embodiments of the invention additionally use a single illumination source to provide light used for TIR measurements and for tissue-image measurements, thereby realizing efficiencies in the combination.

Skin composition and structure is very distinct, very complex, and varies from person to person. By performing optical measurements of the spatio-spectral properties of skin and underlying tissue, a number of assessments may be made. For example, a biometric-identification function may be performed to identify or verify whose skin is being measured, a liveness function may be performed to assure that the sample being measured is live and viable skin and not another type of material, estimates may be made of a variety of physiological parameters such as age gender, ethnicity, and other demographic and anthropometric characteristics, and/or measurements may be made of the concentrations of various analytes and parameters including alcohol, glucose, degrees of blood perfusion and oxygenation, biliruben, cholesterol, urea, and the like.

The complex structure of skin may be used in different embodiments to tailor aspects of the methods and systems for particular functions. The outermost layer of skin, the epidermis, is supported by the underlying dermis and hypodermis. The epidermis itself may have five identified sublayers that include the stratum corneum, the stratum lucidum, the stratum granulosum, the stratum spinosum, and the stratum germinativum. Thus, for example, the skin below the top-most stratum corneum has some characteristics that relate to the surface topography, as well as some characteristics that change with depth into the skin. While the blood supply to skin exists in the dermal layer, the dermis has protrusions into the epidermis known as "dermal papillae," which bring the blood supply close to the surface via capillaries. In the volar surfaces of the fingers, this capillary structure follows the structure of the friction ridges on the surface. In other locations on the body, the structure of the capillary bed may be less ordered, but is still characteristic of the particular location and person. As well, the topography of the interface between the different layers of skin is quite complex and characteristic of the skin location and the person.

A general overview of methods of the invention is provided with the flow diagram of FIG. 1. This figure includes a number of aspects that may or may not be included in certain specific embodiments, and the ordering of blocks in the diagram is not intended to specify a required order since other orderings may be used in alternative embodiments. At block 104, a skin site of an individual is illuminated with light. In some instances, the wavelength range of the illumination light is based on the sensitivity of silicon detector arrays to wavelengths in a range of about 350-1200 nm. Wavelengths less than 600 nm are advantageously emphasize blood features and are therefore preferred in certain embodiments. In other embodiments where images with relatively smooth features are desired, wavelengths longer than approximately 600 nm may be advantageously employed. While the skin site is frequently a fingertip, other skin sites may be used in alternative embodiments, including particularly other regions of the fingers, the palm, and other regions of the hand.

As indicated at blocks 108 and 112, some embodiments may provide the illumination light at multiple wavelengths and/or the light may be provided under different polarization conditions. Such variations in illumination light may advantageously allow collection of information that permits more accurate biometric conclusions to be drawn, including more accurate identity assessments, liveness assessments, and the like. The use of crossed polarization during one or more imaging states tends to emphasize subsurface features and the use of parallel polarization during one or more imaging states tends to emphasize surface features. The polarization may thus be used differently in applications where emphasis of different features is desirable. In cases where linear polarizers are used to polarize the light, "crossed" or "orthogonal" refers to states in which polarization axes are arranged to be approximately at 90° to each other. In cases where circular polarizers are used to polarize the light, "crossed" or "orthogonal" refers to states in which different senses (right-hand or left-hand) of circular polarization are used. The use of linear polarization advantageously provides relatively wide spectral bandwidth at relatively low cost.

Light reflected from the skin site and scattered off and within the underlying tissue may be collected at blocks 116 and 120 to form TIR and tissue images. The images may then be combined at block 124 to form a composite result used in biometric applications. In some instances, information drawn from the TIR and tissue images may be used separately for different purposes. For instance, the tissue image may be used to verify a positive liveness state of tissue while the TIR image is used for identity verification. As another example, the tissue image may be used for identification or identify verification separate from the TIR image, which may be advantageous in those cases where the TIR image quality is degraded due to non-ideal optical conditions. The information from the TIR and multispectral images may be combined in a number of different ways, such as by simply overlaying resulting images or by performing more complex nonlinear mathematical functions on the collected data. The TIR and tissue images are spatially stable relative to each other and, in some embodiments, may be adjusted to be coregistered physically or through image processing. In some embodiments, features such as minutia points may be extracted from both the tissue and TIR images and combined using mathematical operations such as logical "and," logical "or," or other mathematical operations. These biometric features may then be processed to determine identity using methods known to one of familiarity in the art.

Structures that may be used to illuminate the skin site for collection of the TIR and tissue images include structures that have separate illumination sources for each type of measurement or a combined illumination source for the measurements, and structures that have separate detectors for each type of measurement or a combined detector. Furthermore, different optical arrangements may be used in directing the illumination light and in collecting light even with different combinations of illumination sources and detectors. In embodiments that use separate detectors for collecting reflected or scattered light, one detector, such as the TIR detector, may be arranged to receive light along an axis that has an angle greater than a critical angle defined by a platen-air interface, while the other detector, such as the tissue-image detector, may be arranged to receive light along an axis that has an angle less than the critical angle.

Sometimes the detector is described herein as a "camera," with the term intended to be construed broadly as referring to any device equipped for collecting electromagnetic data. For example, each camera or detector may comprise a single element, a plurality of discrete elements, or an array of elements. The light-detection material may be chosen to be appropriate to the source wavelengths and signal and timing requirements, and may include PbS, PbSe, InSb, InGaAs, MCT, bolometers and micro-bolometer arrays. When light is used in the spectral range of about 350-1200 nm, a suitable camera material is silicon. Similarly, a variety of different sources of light may be used in different embodiments. Monochromatic or quasimonochromatic sources include light-emitting diodes ("LEDs"), laser diodes, and vertical cavity surface emitting lasers ("VCSELs"), among other solid-state optoelectronic devices. Broadband sources, which may sometimes be combined with filtering elements or optical shutters, include quartz tungsten halogen incandescent bulbs, and a variety of other broadband optical sources.

Figure 2:
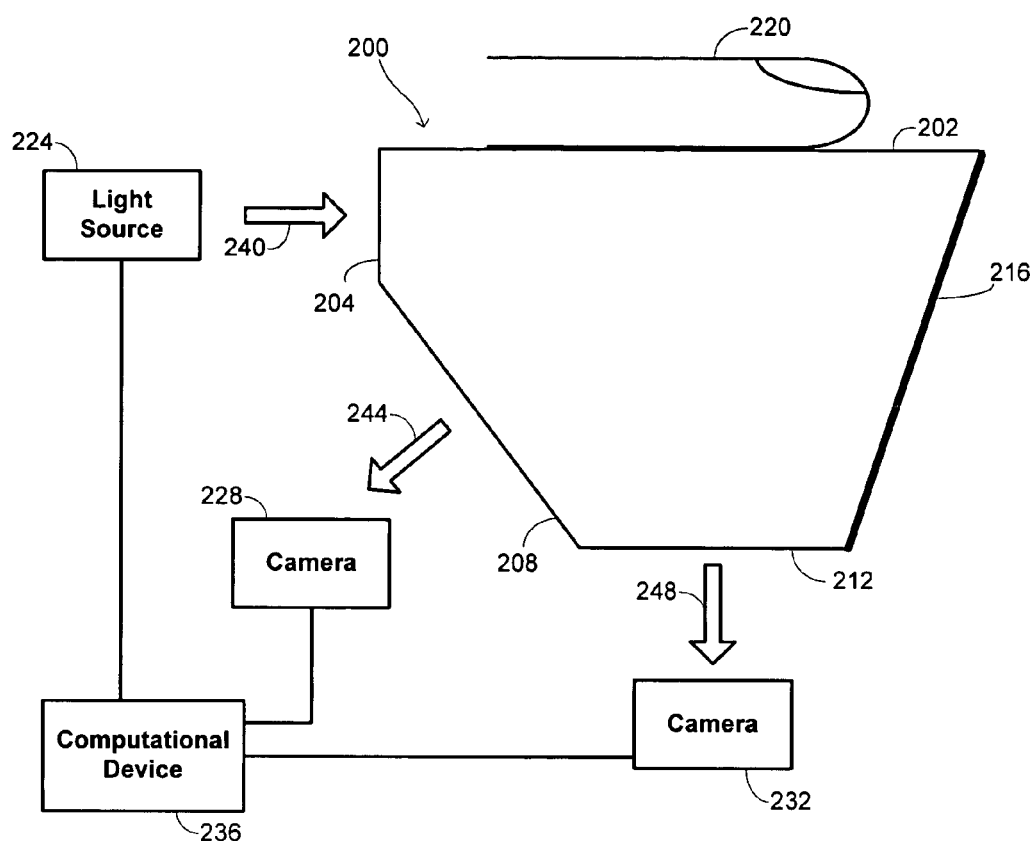
FIG. 2 is a schematic illustration of a system according to one embodiment.

One specific structure that uses two cameras and is suitable for bright-field TIR imaging is shown schematically in FIG. 2. This embodiment uses a single light source 224 that provides illumination light 240 to an optical arrangement 200 to direct the illumination light to a platen over which the skin site is placed. In the drawing, the skin site is illustrated as the surface of a finger 220, although as previously noted other skin sites may be used in other embodiments. The optical arrangement is shown in the form of a prism 200, although alternative embodiments may use an equivalent arrangement of reflectors such as mirrors, or may use a combination of reflectors and prisms. The top surface 202 of the prism acts as the platen to interface with the skin site in this embodiment. The illumination light 240, which may be substantially monochromatic or may by polychromatic in different embodiments, is provided at facet 204 of the prism 200. Camera 228 may be a camera for collecting light 244 to provide a TIR image from facet 208 and camera 232 may be camera for collecting light 248 from facet 212 to provide a tissue image. The light source 224 and cameras 228 and 232 may be interfaced with a computational device 236 that coordinates operation of these components of the system and which may perform analyses on the received TIR and tissue images.

The illumination light 240 impinges on a diffuse reflective coating provided at facet 216, which is useful in bright-field TIR imaging to respond to an illuminated diffuse field. The fingerprint image is formed by points where tissue makes optical contact with the platen and absorbs light, leaving dark patterns. In some embodiments, illumination light may also be provided at facet 212 to enable the collection of additional images.

Either or both of facets 204 and 216 may additionally include a polarizer coating in some embodiments. If provided at facet 204, the polarizer coating may be a partial coating for just certain illuminators. If provided at facet 216, the polarizer coating is preferably deposited to precede the diffuse reflector along optical paths so that light encounters the prism, followed by the polarizer, followed by the diffuse reflector. In embodiments where the polarizer coating provides linear polarization, the linear polarizer is preferably oriented to be substantially perpendicular to the plane of the drawing, thereby accommodating effects resulting from Bragg reflection phenomena. As previously noted, providing an orthogonal polarization on the illumination side then acts to emphasize deep-tissue imaging while providing a parallel polarization on the illumination side then acts to emphasize surface reflections. Certain arrangements may be used to collect both types of images, such as by using different polarizers to provide different polarization states of different illumination sources. Alternatively, a rotatable polarizer may be provided on the illumination side, such as over the light source 224, allowing sequential images to be taken with the illumination-side polarizer in different positions. Equivalently, a rotatable polarizer may be deployed in the detection side to achieve substantially the same result.

Figure 3:
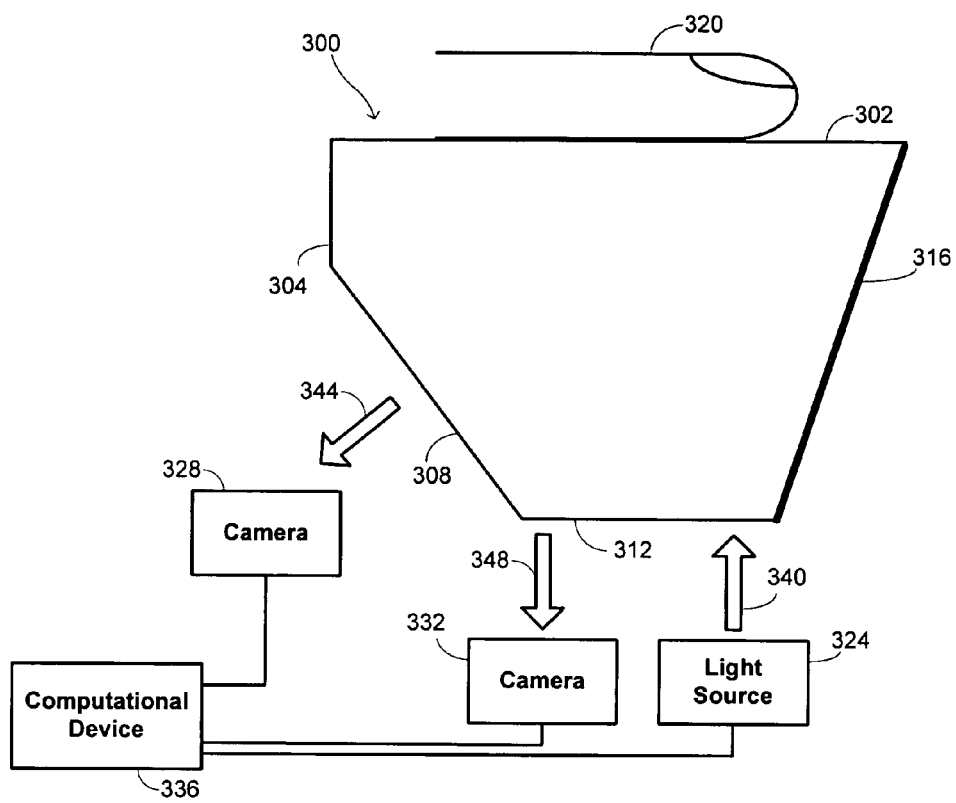
FIG. 3 is a schematic illustration of a system according to another embodiment.

An alternative arrangement suitable for dark-field TIR imaging is illustrated with the schematic drawing of FIG. 3. The overall structure of the arrangement appears similar to that of FIG. 2, with a prism 300 being used to provide optical paths from an illumination source 324 and having a surface 302 that acts as a platen interface with a skin site such as provided by a finger 320. In this embodiment, illumination light 340 is provided at facet 312 and facet 304 may be eliminated, either in the illustrated embodiment or in optical equivalents. Facet 316 may be coated with a light-absorbing material so that the TIR imaging responds to a dark field. The fingerprint image is formed by light being absorbed by tissue and re-emitted at angles greater than the critical angle defined by the platen/air interface, thus providing illuminated patterns where the skin is in contact with the platen 302.

Camera 328 is disposed to receive light 344 emanating from facet 308 to generate a TIR image, and camera 332 is disposed to receive light emanating from facet 312 to generate the tissue image. Again, each of these cameras 328 and 332 and the illumination source 324 are provided in communication with a computational unit 336 that may coordinate operation of the different components and may perform analyses on the received images to complete biometric identifications, determination of liveness, and the like. The specific structures for the light source 324 and for each of the cameras 328 and 332 may take a variety of forms as described above, and the light that is provided may be substantially monochromatic or may be polychromatic in different embodiments.

In some instances, polarization may be used to discriminate different types of features, such as by providing a polarized coating to the light source 340, to facet 312, or to an intermediate optical component like a filter. Similar to other embodiments, a partial coating may be applied in some instances for certain of the illuminators and different polarization conditions may thereby be provided for different illuminators. With the configuration shown in FIG. 3, such an arrangement does not introduce Bragg effects. Parallel-polarization configurations will emphasize surface effects and perpendicular-polarization conditions with emphasize deeper tissue effects. Some embodiment permit the collection of images with different polarization states by providing a rotatable polarizer.

The ability to provide different image conditions, such as different polarization states, different wavelengths, and to collect images at different times permits a greater range of information to be collected. For example, images returned from the TIR camera 328 and from the tissue image camera 332 may be analyzed for subsurface optical effects under multiple conditions. Nominally, each camera collects the same information apart from angular effects, but the TIR image has a TIR mask superimposed on the deep-tissue image. This capability may be used to accommodate perfusion changes, for which certain wavelengths are generally preferred, especially those shorter than about 600 nm. Wavelengths at the peak absorbance features of oxygenated hemoglobin, i.e. at about 540 and 576 nm, may be used in some such embodiments.

Figure 4:
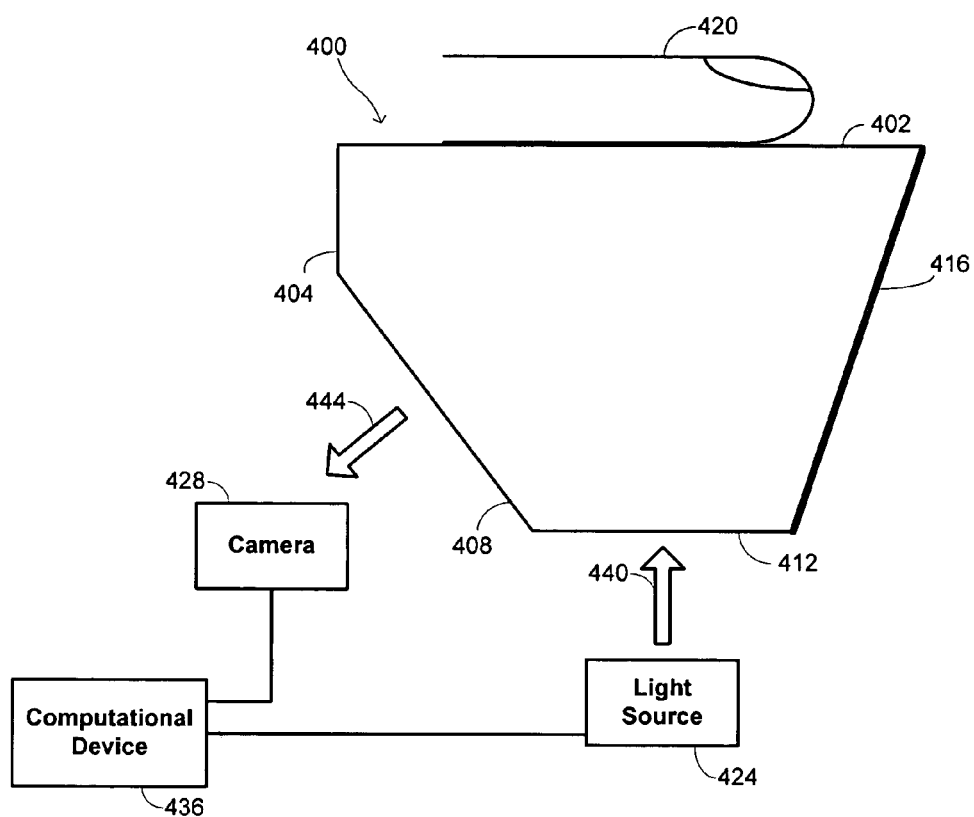
FIG. 4 is a schematic illustration of a system according to a further embodiment.

Another alternative arrangement suitable for dark-field TIR imaging but using only a single camera is illustrated schematically in FIG. 4. This arrangement is similar in some respects to the dark-field TIR arrangement, with a prism 400 being used to provide optical paths from an illumination source 424 and having a surface 402 that acts as a platen interface with a skin site such as may be provided by a finger 420. The illumination light 440 is provided at facet 412 with a light source 424 that may be substantially monochromatic or polychromatic in different embodiments. Facet 416 is coated with a light-absorbing coating so that the TIR imaging responds to a dark field in the same fashion as described in connection with FIG. 3. That is, the fingerprint image is formed by light being absorbed by tissue and re-emitted at angles greater than the critical angle defined by the plate/air interface. The TIR image is formed with light 444 received by camera 428 through facet 408. As is evident from the geometry illustrated in the drawing, facet 404 may be eliminated, either with the configuration as shown or in equivalent optical arrangements. The camera 428 and light source 424 are interfaced with a computational unit 436 programmed to coordinate operation of the system components and/or to perform analyses of the received TIR images.

In embodiments like those shown in FIG. 4, an explicit tissue imaging camera may be omitted, with tissue analysis under different conditions being instead performed just on the ridges that are illuminated in the TIR image. In some instances, light may be polarized in the same fashion as described in connection with FIG. 3 to emphasize surface or deeper tissue effects. In addition, different images may be collected under different image conditions, such as different polarization conditions, with different wavelengths of light, at different times, and the like.

In any of the embodiments shown in FIGS. 2-4, it may sometimes be desirable to incorporate an optical reference material somewhere in the image area to be used in performing calibration functions. Such calibrations may account for changes in light source intensity, gain, detector responsivity, and the like. One simple way in which the calibration may be performed is to use pixel values from the region with the optical reference material to normalize the rest of each color mage by taking a ratio of the image value to the reference value. Other calibration techniques may also be used in different embodiments. A suitable optical reference material is Spectralon®, which is a diffuse reflective coating made by LabSphere. Other optical reference materials that may be used include cardboard reflectance standards such as are commonly used for photography, diffuse white or gray plastics, and the like. More generally, any material that is optically stable over time, reflects a similar amount of light as a real skin site, and is approximately uniform may be used. It is desirable for the optical reference material to provide a measurable signal without saturating the detector.

Figure 5:
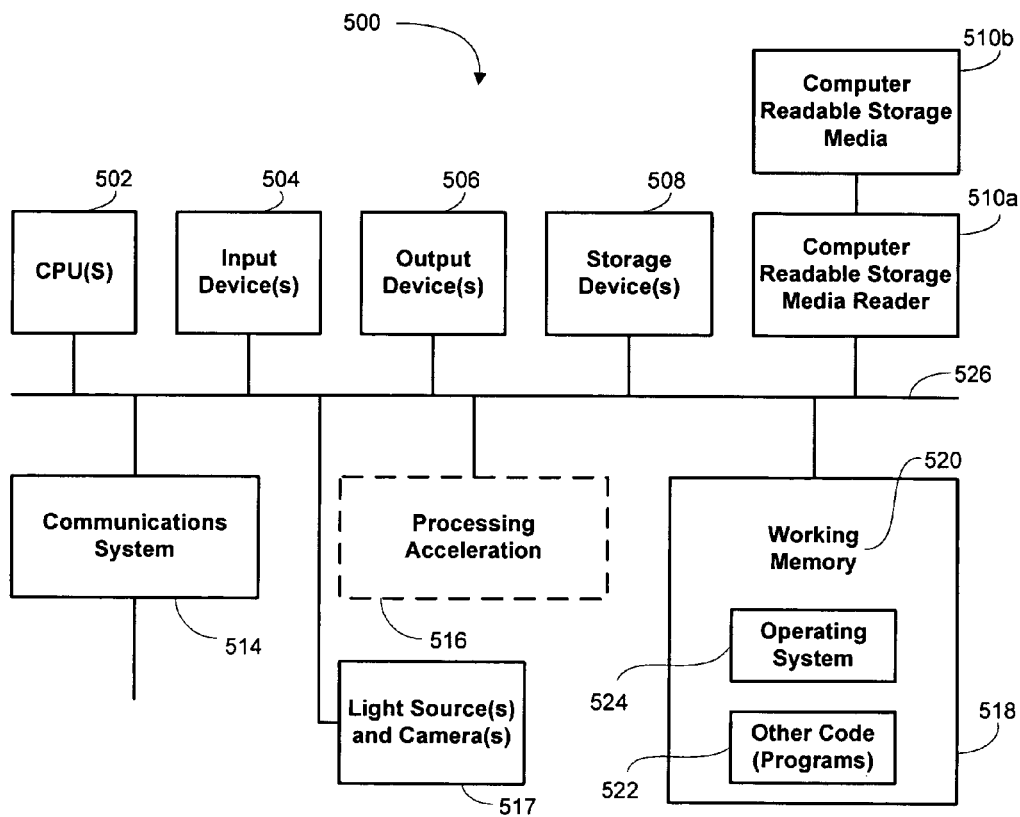
FIG. 5 is a schematic illustration of a computer system that may be used to implement methods of the invention with the systems of FIGS. 2-4.

FIG. 5 broadly illustrates a structure that may be used for the computational devices 236, 336, or 436 used in combination with other system elements. Individual system elements may be implemented in a separated or more integrated manner. The computational device is designated generically by reference number 500 and is shown comprised of hardware elements that are electrically coupled via bus 526, which is also coupled with the light source(s) and camera(s), denoted collectively by reference number 517. The hardware elements include a processor 502, an input device 504, an output device 506, a storage device 508, a computer-readable storage media reader 510*a*, a communications system 514, a processing acceleration unit 516 such as a DSP or special-purpose processor, and a memory 518. The computer-readable storage media reader 510*a* is further connected to a computer-readable storage medium 510*b*, the combination comprehensively representing remote, local, fixed, and/or removable storage devices plus storage media for temporarily and/or more permanently containing computer-readable information. The communications system 514 may comprise a wired, wireless, modem, and/or other type of interfacing connection and permits data to be exchanged with external devices.

The computational device 500 also comprises software elements, shown as being currently located within working memory 520, including an operating system 524 and other code 522, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

Figure 6:
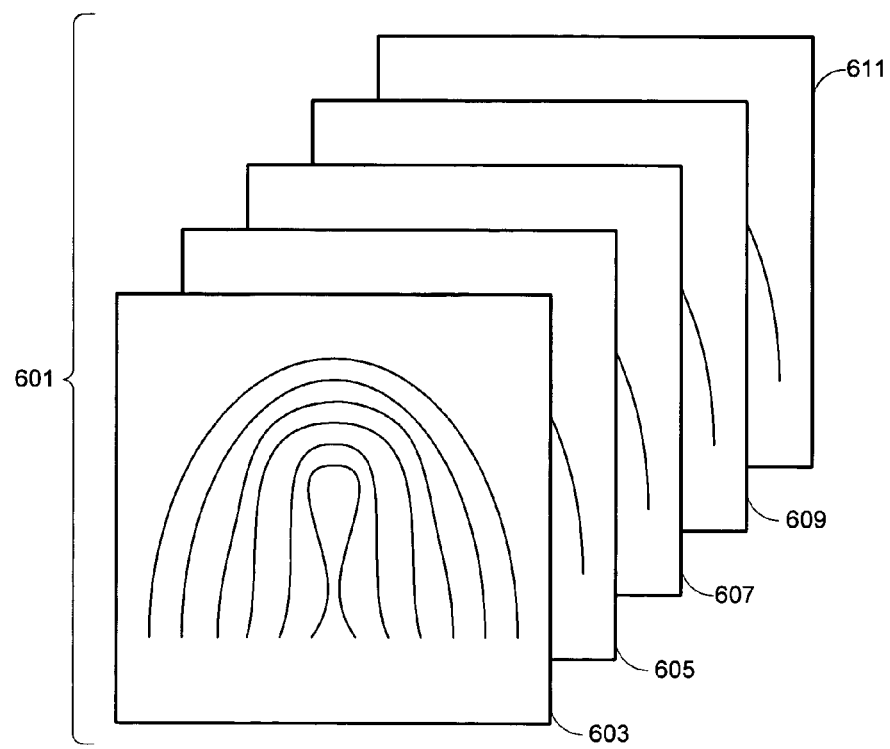
FIG. 6 illustrates a multispectral datacube generated in accordance with embodiments of the invention.

The embodiments described above produce a set of images of the skin site at different wavelengths and/or polarization conditions, or produce data from which such a set may be produced using reconstruction techniques, such as in the particular case of computed tomographic imaging spectrometer or other encoded illumination/detection subsystems. For purposes of illustration, the following discussion is made with reference to such a set of spectral images, although it in not necessary to produce them for subsequent biometric processing in those embodiments that do not generate them directly. An illustrative set of multispectral images is shown in FIG. 6, with the set defining a multispectral datacube 601.

One way to decompose the datacube 601 is into images that correspond to each of the wavelengths and/or polarization conditions used in illuminating the sample in the measurement process. In the figure, five separate images 603, 605, 607, 609, and 611 are shown, corresponding to five discrete illumination wavelengths and/or illumination conditions (e.g. the illumination can be described as a set of secondary point sources of some intensity at the platen surface in positions X, Y and angle α; illumination polarization state P). Similar nomenclature can be used to describe the detection side of the sensor. In an embodiment where visible light is used, the images might correspond, for example, to images generated using light at 450 nm, 500 nm, 550 nm, 600 nm, and 650 nm. Each image represents the optical effects of light of a particular wavelength interacting with skin and, in the case of embodiments where the skin is in contact with a platen during measurement, represents the combined optical effects of light of a particular wavelength interacting with skin and also passing through the skin-platen interface. Due to the optical properties of skin and skin components that vary by wavelength, each of the multispectral images 603, 605, 607, 609, and 611 will be, in general, different from the others. For example, wavelengths shorter than approximately 600 nm are strongly absorbed by blood with peak absorbances at approximately 540 and 576 nm. Images at these wavelengths show blood features strongly, including blanching of the finger as it is pressed against the sensor surface, and a mottled pattern due in part to deeper blood vessels. Light sources of wavelengths longer than approximately 600 nm are less sensitive to blood and are much more smooth and uniform in nature.

The datacube may thus be expressed as $R(X_S, Y_S, \alpha_S, P_S, X_I, Y_I, \alpha_I, P_I, \lambda)$ and describes the amount of light of wavelength $\lambda$ seen at each image point $X_I, Y_I$ at an angle of $\alpha_I$ and viewed through a polarizing element described by $P_I$ when illuminated at a secondary source point described by $X_S, Y_S, \alpha_S, \beta_S$. Different illumination configurations (flood, line, etc.) can be summarized by summing the point response over appropriate secondary source point locations. The multispectral datacube R is related to both conventional fingerprint images and to spectral biometric datasets, containing information about each of these biometric modalities. The multispectral datacube R is a superset of either of the other two data sets and contains correlations and other information that may be lost in either of the two separate modalities.

The optical interactions at the skin-platen interface due to TIR effects will be substantially the same at all wavelengths since the optical index of refraction of the platen material and the skin are not generally significantly different over the range of wavelengths used. However, the tissue image will generally be affected by factors such as different wavelengths, different polarization conditions, different illumination and detection angles, and other factors that define different optical conditions and comprise the multispectral conditions.

The multispectral image datacube contains spatio-spectral information from multiple sources. Merely by way of example, for the case of a measurement taken on the fingertip in contact with a platen, the resulting datacube contains effects due to: (i) the optical interface between the fingertip and the platen, similar to information contained in a conventional non-TIR fingerprint; (ii) the overall spectral characteristics of the tissue, which are distinct from person to person; (iii) the blood vessels close to the surface of the skin, and especially the capillaries that lie directly below the friction ridges that make up the external fingerprint pattern; and (iv) the blood vessels and other spectrally active structures distributed deeper in the tissue, in a manner similar to vein imaging. As such, embodiments of the invention provide a mechanism for extracting biometric data from multiple sources within the fingertip or other skin site being measured, thereby providing multifactor biometric-sensing applications.

Because of the complex wavelength-dependent properties of skin and underlying tissue, the set of spectral values corresponding to a given image location has spectral characteristics that are well-defined and distinct. These spectral characteristics may be used to classify the multispectral image data on a pixel-by-pixel basis. This assessment may be performed by generating typical tissue spectral qualities from a set of qualified images. For example, the multispectral data shown in FIG. 6 may be reordered as an N×5 matrix, where N is the number of image pixels that contain data from living tissue, rather than from a surrounding region of air. An eigenanalysis or other factor analysis performed on this set matrix produces the representative spectral features of these tissue pixels. The spectra of pixels in a later data set may then be compared to such previously established spectral features using metrics such as Mahalanobis distance and spectral residuals. If more than a small number of image pixels have spectral qualities that are inconsistent with living tissue, then the sample is deemed to be non-genuine and rejected, thus providing a mechanism for incorporating antispoofing methods in the sensor based on determinations of the liveness of the sample.

Similarly, in an embodiment where the sample is a fingertip, the multispectral image pixels are classified as "ridge," "valley," or "other," based on their spectral qualities. This classification can be performed using discriminant analysis methods such as linear discriminant analysis, quadratic discriminant analysis, principle component analysis, neural networks, and others known to those of skill in the art. Since ridge and valley pixels are contiguous on a typical fingertip, in some instances multispectral data from the local neighborhood around the image pixel of interest are used to classify the image pixel. In this way, a conventional fingerprint image is extracted from the sensor for further processing and biometric assessment. The "other" category may indicate image pixels that have spectral qualities that are different than anticipated in a genuine sample. A threshold on the total number of pixels in an image classified as "other" may be set. If this threshold is exceeded, the sample may be determined to be non-genuine and appropriate indications made and actions taken.

Figure 7A:
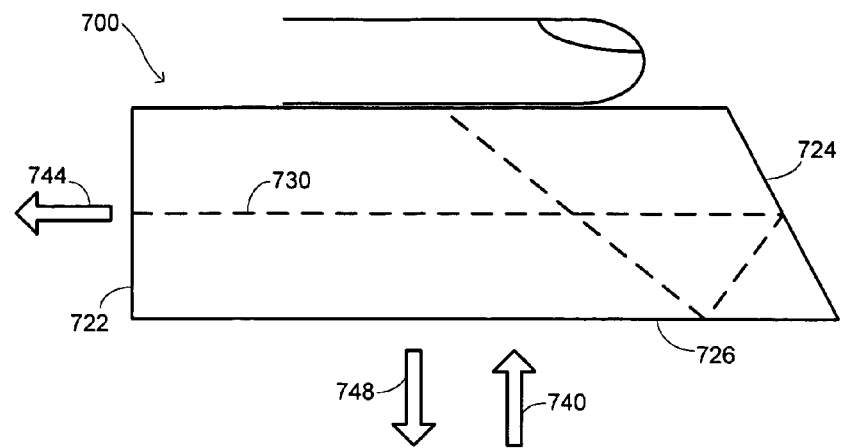
FIGS. 7A and 7B provide schematic illustrations of alternative arrangements that may be used with the systems of FIGS. 2 and 3.
Figure 7B:
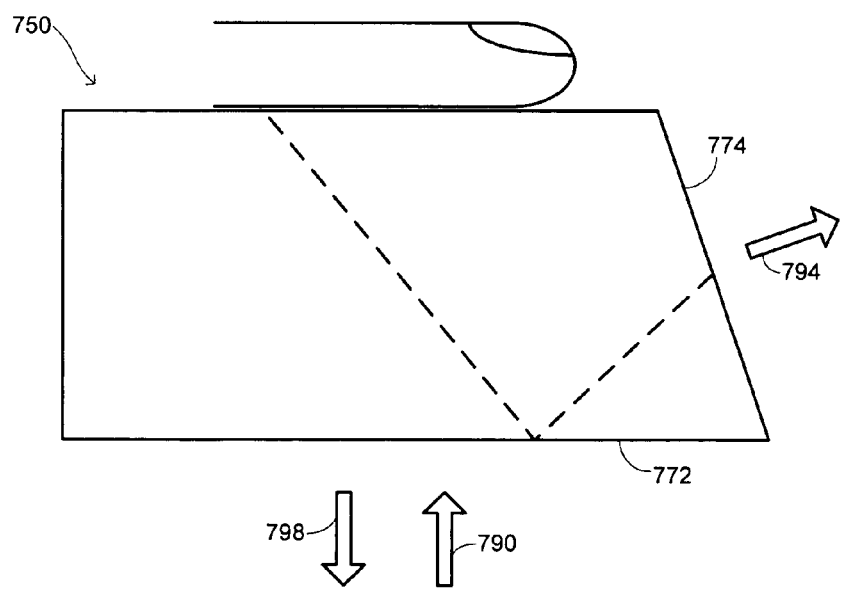

While numerous alternative optical configurations may be used without exceeding the intended scope of the invention, FIGS. 7A and 7B are provided to illustrate examples of alternative configurations that may be used with the embodiments described in connection with FIGS. 2-4. FIG. 7A shows a prism 700 that is used that may provide optical paths as illustrated with the dashed line 730. Illumination light 740 is provided at facet 726 and facet 724 has a reflective coating that may include optical power by being shaped to aid focusing of the image. Light 744 used in forming the TIR image is received from facet 722 and in those embodiments where a second camera is used for the tissue image, i.e. similar to FIGS. 2 and 3, light 748 used in forming the tissue image may be received from facet 726.

FIG. 7B shows a configuration that is similar by providing a prism 750 with illumination light incident on facet 772, but differs by having no reflective coating on facet 774. Light 794 used in forming the TIR image is thus received from facet 774, and in those embodiments where a second camera is used for the tissue image, i.e. similar to FIGS. 2 and 3, light 798 used in forming the tissue image is received from facet 772. The alternative embodiments illustrated in FIGS. 7A and 7B may be configured in a variety of different ways that have already been described generally in connection with FIGS. 2-4, including providing different polarization conditions, using substantially monochromatic or polychromatic light, and the like.

There are, furthermore, a number of different ways in which data collected by the camera(s) in the different embodiments may be processed. The dark-field TIR images generated by systems such as those depicted in FIGS. 3 and 4 may be processed in different ways in embodiments that have a single camera or in embodiments that have multiple cameras, and information drawn from the TIR images may be coupled with information drawn from the tissue images. For instance, an assessment may be made of pixels along ridges identified in the TIR image to ensure that the spectral characteristics are consistent with living tissue. When multiple images are taken over time, changes in the pixels along the ridges may be assessed to ensure that perfusion changes expected with living tissue are observed. In addition, difference images may be generated for multiple polarization states and/or multiple illumination wavelengths to ensure that the results are consistent with living tissue. In addition to these liveness tests, intensity differences (spatially and with respect to multiple wavelengths, polarization states, and/or illumination and detection angles) along the ridges may be examined as part of an identification process to ensure that they are consistent with intensity differences observed during an enrollment process. These ridge intensity differences are affected in part by underlying skin structures.

In instances where two cameras are used to additionally collect tissue image data, a variety of image-processing techniques may be used to analyze the image data, including edge-detection and image-enhancement techniques. Examples of edge-detection techniques that may be used include Laplacian of Gaussian, Sobel, Prewitt, and other techniques known to those of skill in the art. In some instances, a linear or nonlinear model relating tissue-image features to TIR features may be created, with the model being used to predict missing portions of the TIR image. The availability of two types of image measurements also permits biometric functions to be performed more robustly by using dual biometric sensing. Each of the different images includes information drawn from the same portion of the body at the same time, and the combination is therefore resistant to being defeated by using different samples or different techniques to defeat the different image measurements. The system is thus generally resistant to a variety of different types of spoofing. Furthermore, the tissue data may be assessed directly for spoof detection by performing a liveness assessment. This may include performing a spectral assessment of the image, checking that subsurface patterns, especially blood patterns, match data that were collected as part of an enrollment function, and ensuring that the fingerprint patterns of the TIR and tissue images are consistent.

Examples of images collected with a system of the invention are illustrated with FIGS. 8A-9C. FIGS. 8A-8C show images collected from a subject at a fingertip skin site, with the tissue image being collected with three illumination colors (green, red, and blue). The TIR fingerprint image is shown in FIG. 8A, the tissue image is shown in FIG. 8C, with the two being overlaid in FIG. 8B. It is apparent that the tissue image provides a greater area of coverage relative to the corresponding TIR image and that the combination of the two synergistically provides information not available from either image alone. The mottled pattern of the tissue image in FIG. 8C is an example of nonfingerprint features that can be measured and which are of interest in biometric applications.

The sequence of FIGS. 9A-9C is similar to the sequence of FIGS. 8A-8C, but were collected when a piece of transparent tape was applied to the fingertip prior to imaging. While the TIR image of FIG. 9A is clearly degraded because of the presence of the tape, the tissue image of FIG. 9C shows almost no degradation. When the images are combined, as shown in FIG. 9B, it is evident that the inclusion of the tissue image permits the system to collect useful data in regions that a TIR image alone would be unable to collect.

FIG. 10 provides an example of a tissue image collected when the sensor includes optical reference material, in this instance as thin pieces of material 002 and 1004 that run along edges of the image. As described above, the presence of this material permits calibrations to be performed on the image to account for changes in conditions, such as may arise from changes in the intensity of light sources, changes in detector sensitivity, and the like. The calibrations are performed by using pixel values in the region of the optical reference material to normalize the remainder of the image.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A system for performing a biometric function, the system comprising:
   an illumination source;
   a platen disposed to make contact with a skin site of an individual;
   a light detector;
   an optical train disposed to provide optical paths between the illumination source and the platen and to provide optical paths between the platen and the light detector, wherein the combination of the illumination source and optical train provides illumination to the platen under multispectral conditions;
   a computational unit interfaced with the light detector and having instructions to generate a total-internal-reflectance image of the skin site from a first portion of light received from the skin site and to generate a multispectral tissue image of the skin site from a second portion of light received from the skin site; and
   determining a liveness state of tissue at the skin site from the multispectral tissue image.

2. The system recited in claim 1 wherein the illumination source is a polychromatic illumination source.

3. The system recited in claim 1 wherein the optical train comprises a prism having a plurality of facets, the illumination source disposed to provide illumination light to a first of the facets and the light detector disposed to receive light from a second of the facets.

4. The system recited in claim 3 wherein the first and second facets are the same facet.

5. The system recited in claim 3 wherein:
the light detector comprises a first light detector disposed to receive the first portion of light through the second facet and a second light detector disposed to receive the second portion of light from a third facet;
the second facet is substantially orthogonal to a first axis having an angle with the platen greater than a critical angle $\theta_c$ of an interface of the platen with air; and
the third facet is substantially orthogonal to a second axis having an angle with the platen less than the critical angle $\theta_c$.

6. The system recited in claim 5 wherein the first, second, and third facets are different facets.

7. The system recited in claim 6 further comprising a diffuse reflector disposed on a fourth facet different from the first, second, and third facets.

8. The system recited in claim 5 further comprising a light absorber disposed on a fourth facet different from the first, second, and third facets.

9. The system recited in claim 1 wherein the optical train comprises polarizers disposed to polarize light incident on the skin site and to polarize light received by the light detector.

10. The system recited in claim 9 wherein the polarizers are oriented such that light incident on the skin site and the light received by the light detector have substantially parallel polarizations.

11. The system recited in claim 9 wherein the polarizers are oriented such that light incident on the skin site and the light received by the light detector have substantially orthogonal polarizations.

12. A method for performing a biometric function, the method comprising:
illuminating a skin site of an individual under multispectral conditions;
receiving light from the skin site;
generating a total-internal-reflectance image of the skin site from a first portion of the received light;
generating a multispectral tissue image of the skin site from a second portion of the received light; and
determining a liveness state of tissue at the skin site from the multispectral tissue image.

13. The method recited in claim 12 wherein illuminating the skin site comprises illuminating the skin site with a single illumination source.

14. The method recited in claim 12 wherein illuminating the skin site comprises illuminating the skin site with polychromatic light.

15. The method recited in claim 12 wherein:
illuminating the skin site comprises:
generating light; and
directing the generated light to the skin site and to a diffuse reflector to provide a diffuse light field; and
generating the total-internal-reflectance image of the skin site comprises identifying dark patterns corresponding to positions where the skin site makes optical contact with the light and absorbs light.

16. The method recited in claim 12 wherein:
illuminating the skin site comprises:
generating light; and
directing the generated light to the skin site and to a light absorber; and
generating the total-internal-reflectance image of the skin site comprises identifying illuminated patterns corresponding to positions where the skin site makes optical contact with the light and re-emits light.

17. The method recited in claim 12 wherein:
the skin site is in contact with a platen that defines a platen-air interface having a critical angle $\theta_c$;
receiving light from the skin site comprises:
receiving the first portion of the light with a first light detector disposed on a first axis having an angle with the platen-air interface greater than $\theta_c$; and
receiving the second portion of the light with a second light detector disposed on a second axis having an angle with the platen-air interface less than $\theta_c$.

18. The method recited in claim 12 wherein illuminating the skin site of the individual comprises polarizing generated light, the method further comprising polarizing the second portion of the received light.

19. The method recited in claim 18 wherein polarizations of the generated light and the second portion of the received light are substantially parallel.

20. The method recited in claim 18 wherein polarizations of the generated light and the second portion of the received light are substantially orthogonal.

21. The method recited in claim 18 wherein the generated light and the second portion of the received light have a first relative polarization, the method comprising repeating the steps of illuminating the skin site, receiving light from the skin site, generating the total-internal-reflectance image, and generating the multispectral tissue image with the generated light and the second portion of the received light having a second relative polarization that differs from the first relative polarization.

22. The method recited in claim 12 wherein:
illuminating the skin site of the individual comprises polarizing generated light; and
receiving light from the skin site comprises polarizing the first portion of the received light with a polarization substantially parallel to a polarization of the generated light.

23. The method recited in claim 12 comprising:
repeating the steps of illuminating the skin site and receiving light from the skin site;
generating a second multispectral tissue image; and
identifying a perfusion change from the second multispectral tissue image.

24. The method recited in claim 12 further comprising verifying an identity of the individual by confirming consistency of the total-internal-reflectance image and of the tissue image with previously collected enrollment data.

25. A method for performing a biometric function, the method comprising:
capturing a first image of a skin site of an individual under a first set of optical conditions;
capturing a second image of the skin site of the individual under a second set of optical conditions different from the first set, wherein a polarization state of the first set of optical conditions is different from a polarization state of the second set of optical conditions and/or wherein light incident on the skin site under the first set of optical conditions has a different wavelength composition than light incident on the skin site under the second set of optical conditions;
using the first and second images to perform the biometric function; and
determining a liveness state of tissue at the skin site from the first and second images.

* * * * *